United States Patent [19]

Lautenschläger et al.

[11] Patent Number: 4,654,358

[45] Date of Patent: * Mar. 31, 1987

[54] 1,4,5-TRIPHENYLIMIDAZOL-2-YL MERCAPTO ALKANOIC ACIDS, USEFUL AGAINST INFLAMMATION AND DISEASES RESPONDING TO LIPID LOWERING

[75] Inventors: Hans-Heiner Lautenschläger, Pulheim-Stommeln; Gerrit Prop, Pulheim; Helmut Wetzig, Pulheim-Sinnersdorf, all of Fed. Rep. of Germany

[73] Assignee: A. Nattermann & Cie GmbH, Cologne, Fed. Rep. of Germany

[*] Notice: The portion of the term of this patent subsequent to Jul. 17, 2001 has been disclaimed.

[21] Appl. No.: 624,012

[22] Filed: Jun. 25, 1984

[30] Foreign Application Priority Data

Jul. 2, 1983 [DE] Fed. Rep. of Germany ....... 3323870

[51] Int. Cl.$^4$ .................. A61K 31/415; C07D 233/84
[52] U.S. Cl. ..................................... 514/398; 548/337
[58] Field of Search .................... 548/337; 424/273 R; 514/398

[56] References Cited

U.S. PATENT DOCUMENTS 3,636,003  1/1972  Doebel et al. ...................... 548/337
4,460,598  7/1984  Lautenschlager et al. ......... 548/337

OTHER PUBLICATIONS

Schacht, Topics in Current Chemistry, 72, pp. 99–123 (1977).
Howe, Atherosclerosis, Report of the Progress in Applied Chemistry, 59, pp. 489–502 (1976).
Chemical Abstracts, vol. 57, 2208–2209.

Primary Examiner—Richard A. Schwartz
Assistant Examiner—Kurt G. Briscoe
Attorney, Agent, or Firm—Pearne, Gordon, McCoy & Granger

[57] ABSTRACT

The invention is related to imidazol-2-yl mercapto alkanoic acids having the formula I

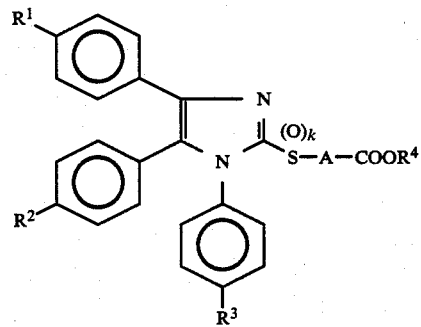

process for the treatment of humans suffering from inflammatory diseases or diseases in relation with the lipid metabolism.

3 Claims, No Drawings.

1,4,5-TRIPHENYLIMIDAZOL-2-YL MERCAPTO ALKANOIC ACIDS, USEFUL AGAINST INFLAMMATION AND DISEASES RESPONDING TO LIPID LOWERING

The invention is related to imidazol-2-yl mercapto alkanoic acids and process for the treatment of humans suffering from certain diseases, i.e. inflammatory diseases and in particular diseases in relation with their lipid metabolism or hyperlipidemic states.

The compounds according to the invention correspond to the formula I

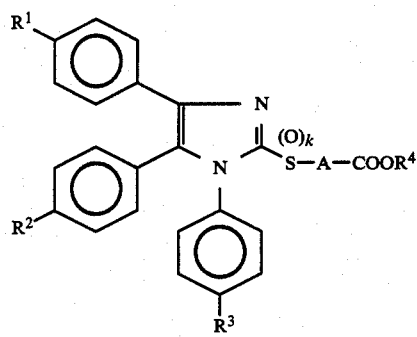

wherein
k is the numeral 0, 1 or 2,
$R^1$, $R^2$ and $R^3$ which are the same or different from each other, are a member selected from the group consisting of hydrogen, fluorine, chlorine, methyl, methoxy and trifluoromethyl,
$R^4$ is a member selected from the group consisting of hydrogen, sodium, potassium, methyl, ethyl, propyl, isopropyl and butyl, and
A is a member selected from the group consisting of the groups

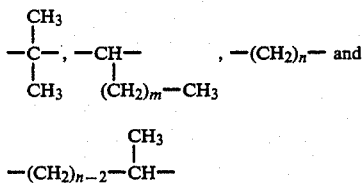

wherein m is zero or a numeral from 1 to 8 and n is a numeral from 2 to 10.

Particularly preferred are those compounds of formula I, wherein A is the group —$(CH_2)_3$— or

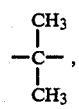

while k, $R^1$, $R^2$, $R^3$ and $R^4$ have the same meaning as above given in formula I.

Compounds according to invention are for instance:
3-(1.4.5-triphenylimidazol-2-yl mercapto)propionic acid
4-(1.4.5-triphenylimidazol-2-yl mercapto)butyric acid
5-(1.4.5-triphenylimidazol-2-yl mercapto)valeric acid
6-(1.4.5-triphenylimidazol-2-yl mercapto)capronic acid
7-(1.4.5-triphenylimidazol-2-yl mercapto)enanthic acid;
8-(1.4.5-triphenylimidazol-2-yl mercapto)caprylic acid;
9-(1.4.5-triphenylimidazol-2-yl mercapto)pelargonic acid;
10-(1.4.5-triphenylimidazol-2-yl mercapto)caprinic acid;
11-(1.4.5-triphenylimidazol-2-yl mercapto)undecanoic acid;
4-[4.5-diphenyl-1-(4-methoxyphenyl)-imidazol-2-yl mercapto]butyric acid;
4-[1-(4-chlorophenyl)-4.5-diphenylimidazol-2-yl mercapto]butyric acid;
4-[4.5-diphenyl-1-(4-methylphenyl)imidazol-2-yl mercapto]butyric acid;
4-[4.5-diphenyl-1-(2-fluorophenyl)-imidazol-2-yl mercapto]butyric acid;
4-[4.5-bis-(4-chlorophenyl)-1-phenyl-imidazol-2-yl mercapto]butyric acid;
4-[4.5-bis-(4-fluorophenyl)-1-phenyl-imidazol-2-yl mercapto]butyric acid;
4-[4.5-bis-(4-methoxyphenyl)-1-phenyl-imidazol-2-yl mercapto]butyric acid;
4-[1.4.5-tris-(4-chlorophenyl)-imidazol-2-yl mercapto]butyric acid;
8-[4.5-diphenyl-1-(4-methoxyphenyl)-imidazol-2-yl mercapto]caprylic acid;
8-[1-(4-chlorophenyl)-4.5-diphenylimidazol-2-yl mercapto]caprylic acid;
8-[4.5-diphenyl-1-(4-methylphenyl)-imidazol-2-yl mercapto]caprylic acid;
8-[4.5-diphenyl-1-(2-fluorophenyl)-imidazol-2-yl mercapto]caprylic acid;
8-[4.5-bis-(4-chlorophenyl)-1-phenyl-imidazol-2-yl mercapto]caprylic acid;
8-[4.5-bis-(4-fluorophenyl)-1-phenyl-imidazol-2-yl mercapto]caprylic acid;
8-[4.5-bis-(4-methoxyphenyl)-1-phenyl-imidazol-2-yl mercapto]caprylic acid;
8-[1.4.5-tris-(4-chlorophenyl)-imidazol-2-yl mercapto]caprylic acid;
8-[4.5-diphenyl-1-(4-trifluoromethylphenyl)-imidazol-2-yl mercapto]caprylic acid;
2-(1.4.5-triphenylimidazol-2-yl mercapto)-propionic acid;
2-(1.4.5-triphenylimidazol-2-yl mercapto)-butyric acid;
2-(1.4.5-triphenylimidazol-2-yl mercapto)-valeric acid;
2-(1.4.5-triphenylimidazol-2-yl mercapto)-capronic acid;
2-(1.4.5-triphenylimidazol-2-yl mercapto)-enanthic acid;
2-(1.4.5-triphenylimidazol-2-yl mercapto)-caprylic acid;
2-(1.4.5-triphenylimidazol-2-yl mercapto)-pelargonic acid;
2-(1.4.5-triphenylimidazol-2-yl mercapto)-caprinic acid;
2-(1.4.5-triphenylimidazol-2-yl mercapto)-undecanoic acid;
2-[1-(4-chlorophenyl)-4.5-diphenyl-imidazol-2-yl mercapto]caprinic acid;
2-[4.5-diphenyl-1-(4-methoxyphenyl)imidazol-2-yl mercapto]caprinic acid;
2-[4.5-diphenyl-1-(4-methylphenyl)-imidazol-2-yl mercapto]caprinic acid;
2-[4.5-diphenyl-1-(4-fluorophenyl)-imidazol-2-yl mercapto]caprinic acid;
2-[4.5-bis-(4-chlorophenyl)-1-phenyl-imidazol-2-yl mercapto]caprinic acid;
2-[4.5-bis-(4-fluorophenyl)-1-phenyl-imidazol-2-yl mercapto]caprinic acid;
2-[4.5-bis-(4-methoxyphenyl)-1-phenyl-imidazol-2-yl mercapto]caprinic acid;

2-[1.4.5-tris-(4-chlorophenyl)-imidazol-2-yl mercapto]-caprinic acid;

2-[4.5-diphenyl-1-(4-trifluoromethylphenyl)-imidazol-2-yl mercapto]caprinic acid;

2-methyl-2-(1.4.5-triphenylimidazol-2-yl mercapto)-propionic acid;

2-[4.5-bis-(4-chlorophenyl)-1-phenyl-imidazol-2-yl mercapto]-2-methylpropionic acid;

2-[4.5-bis-(4-methoxyphenyl)-1-phenyl-imidazol-2-yl mercapto]-2-methylpropionic acid;

as well as the corresponding sulfoxides, sulfones, esters and alkali metal salts.

The compounds according to invention show interesting pharmacological properties, in particular a lipid lowering as well a antiinflammatory activity with an excellent compatibility.

The present invention is further directed to processes for the preparation and to pharmaceutical preparations of these compounds and their use as drugs.

The compounds according to the present invention of formula I wherein k=O are produced in that a 4-imidazolin-2-thione of formula II

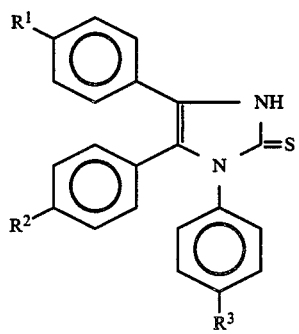

wherein $R^1$, $R^2$ and $R^3$ have the meaning as given in formula I, is converted into the corresponding alkali metal salt by the addition of an auxiliary base such as sodium hydride or potassium hydride, in an inert organic solvent such as dimethylformamide, dimethylacetamide, tetramethylurea, tetrahydro thiophene-1.1-dioxide, and this alkali metal salt is subjected to reaction with an alkylating agent of the formula III

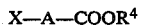

X—A—COOR⁴    III wherein A and $R^4$ have the meaning as given in formula I and X is a halogen, a tosyl group or a similar usual split-off group.

The starting materials of formula II are produced by known processes from the corresponding 4-imidazolin-2-ones by reaction with di-phosphoruspentasulfide in toluene or by reaction with Lawesson reagent or directly from the corresponding benzoines by reaction with phenylthiourea. Esters of formula I may be converted by usual processes, for instance by reaction with an alkali metal hydroxide in aqueous, aqueous-organic or organic solvents such as water, alcohols, ethers or mixtures thereof, into the corresponding alkali metal salts of formula I which may be converted into the corresponding acids of formula I by a subsequent addition of an inorganic acid (mineral acid).

On a contrary way, the esters of formula I may be produced from the acids of formula I and the alkali metal salts of formula I by usual processes, for instance by treating the acids with the corresponding alcohols with the addition of a mineral acid as catalyst or by reesterification with formic or acetic acid esters in the presence of a condensation agent such as dicyclohexyl carbodiimide or by alkylating the alkali metal salts of formula I with the corresponding alkyl halides, alkyl sulfates and the like in inert solvents.

The compounds of formula I wherein k=O may also be prepared in that the starting material II is converted to the halo-derivative of formula IV

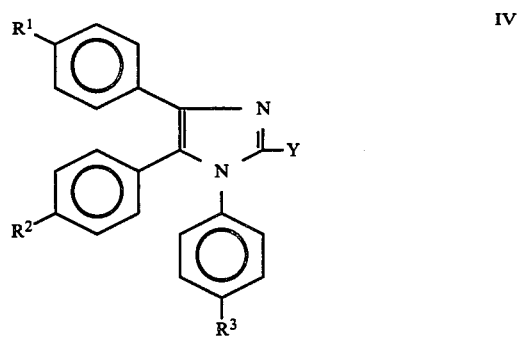

wherein $R^1$, $R^2$ and $R^3$ have the meaning as given in formula I and X is a halogen atom, by means of a halogenating agent such as $POCl_3$ or $PCl_5$ and subsequently subjecting the intermediary products IV, with the addition of an auxiliary base such as alkali metal hydroxide, alkaline earth metal hydroxide, alkali metal hydride, to reaction with a compound of formula V

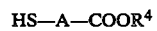

HS—A—COOR⁴    V wherein A and $R^4$ have the meaning as given in formula I, in inert organic solvents such as dimethylformamide, dimethylacetamide, tetramethylurea, alcohols and the like, possibly at elevated pressure. The sulfoxides and sulfones of formula I wherein k is 1 or, respectively, k is 2, are prepared from the mercapto esters wherein k is O, by reaction with oxidizing agents such as with hydrogen peroxide in anhydrous acetic acid or acetone, with sodium metaperiodate/anhydrous acetic acid, potassium permaganate/mineral acid or organic peroxy acids such as m-chloroperbenzoic acid in $CHCl_3$, $CH_2Cl_2$ or similar inert solvents.

The present invention also is related to pharmaceutical preparations which contain the new imidazol-2-yl mercapto alkanoic acids as free acid or as salts with pharmacologically compatible bases or as esters. The pharmaceutical preparations according to the present invention are used for enteral, i.e. oral or rectal or parenteral application. They contain the pharmaceutically active agents as such or together with usual pharmaceutically useful carrier materials. Preferably, the pharmaceutical preparations of the active agent represent single doses corresponding to the desired application such as tablets, dragees, capsules, suppositories, granulates, solutions, emulsions or suspensions. The dosages usually are between 1 and 1000 mg per day, preferably between 10 and 500 mg per day which dose is administered once or several times, preferably twice or three times, per day.

The reported melting points have been measured by means of a Büchi-melting point apparatus and are not corrected. The infrared spektra have been determined with a Nicolet NIC-3600 and the mass spektra with a Varian MAT-311A (70 eV).

EXAMPLE 1

8-(1.4.5-Triphenylimidazol-2-yl mercapto)-octanoic acid methyl ester 13.8 g of an 80% sodium hydride suspension in mineral oil are washed with pentane and are added to a mixture of 153 g of 1.4.5-triphenyl-4-imidazolin-2-thione in 600 cc. of anhydrous dimethylformamide. The mixture is stirred at first at room temperature and then at 60° C. until the end of hydrogen formation. After the addition of 0.5 g of sodium iodide there are added dropwise 109 g of 8-bromooctanoic methyl ester. The resulting mixture is stirred for 4 hours at 60° C., cooled, diluted with water and extracted with chloroform. The chloroform solution is washed with water, dried over sodium sulfate and evaporated. The residue is recrystallized from tetrahydrofuran Yield: 186.2 g F.: 120° to 121° C.
IR (in KBr): 1736 cm$^{-1}$.

EXAMPLE 2

4-(1.4.5-Triphenylimidazol-2-yl mercapto)-butyric acid ethyl ester

Similar to Example 1 from:
4.5 g of an 80% sodium hydride suspension in mineral oil,
50 g of 1.4.5-triphenyl-4-imidazolin-2-thione,
300 cc. of dimethylformamide,
4.5 g of sodium iodide,
23 g of 4-chlorobutyric acid ethyl ester.
Recrystallization of the crude product from ethanol.
Yield: 61 g F.: 118° C.
IR (in KBr): 1732 cm$^{-1}$.

EXAMPLE 3

2-(1.4.5-Triphenylimidazol-2-yl mercapto)-octanoic acid ethyl ester

Similar to Example 1 from:
6.4 g of an 80% sodium hydride suspension in mineral oil,
63.3 g of 1.4.5-triphenyl-4-imidazolin-2-thione,
200 cc. of dimethylformamide,
39 g of 2-bromooctanoic acid ethyl ester.
The mixture is stirred for 4 hours at 150° C. Purification of the crude product by column chromatography (silicic acid gel//hexane/acetic acid ethyl ester).
Yield: 61.5 g F.: 88° C.
IR (in KBr): 1734 cm$^{-1}$.

EXAMPLE 4

2-Methyl-2-(1.4.5-triphenylimidazol-2-yl mercapto)-propionic acid ethyl ester

Similar to Example 1 from:
8.3 g of 80% sodium hydride suspension in mineral oil,
92.5 g of 1.4.5-triphenyl-4-imidazolin-2-thione,
300 cc. of dimethylformamide,
8.4 g of sodium iodide,
55 g of 2-bromoisobutyric acid ethyl ester.
The mixture is stirred for 2 hours at 80° C. Recrystallization of the crude product from acetic acid ethyl ester.
Yield: 92 g F.: 167°–169° C.
IR (in KBr): 1728 cm$^{-1}$.
MS [m/e]: 442 (74%), 328 (100%), 269 (82%).

EXAMPLE 5

8-(1.4.5-Triphenylimidazol-2-yl mercapto)-octanoic acid 170 g of 8-(1.4.5-triphenylimidazol-2-yl mercapto)-octanoic acid methyl ester are dissolved in 1.2 l of tetrahydrofurane. 42 g of sodium hydride dissolved in 700 cc. of methanol are added thereto. The mixture is stirred 24 hours at 40° to 50° C., cooled, diluted with about 2 l of water and acidified with delute hydrochloric acid. The crude acid is filtered off, dried and recrystallized from toluene.

Yield: 151 g F.: 150° to 152° C.
IR (in KBr): 1701 cm$^{-1}$..
MS [m/e]: 470(56%), 423(21%), 328(100%), 269(22%), 252 (10%).

EXAMPLE 6

4-(1.4.5-Triphenylimidazol-2-yl mercapto)-butyric acid 80 g of 4-(1.4.5-triphenylimidazol-2-yl mercapto)-butyric acid ethyl ester are dissolved in 700 cc. of ethanol at 80° C. 22 g of sodium hydroxide dissolved in 200 cc. of ethanol are added thereto and the mixture is stirred for 3 hours at 80° C. The solvent is distilled off, the residue is washed with ether and acidified with dilute hydrochloric acid. The resulting acid is triturated in chloroform, the chloroform solution is washed with water, dried over sodium sulfate and the solvent is distilled off.

Yield: 73 g F.: 165° C.
MS[m/e]: 414 (100%), 328 (69%), 269(36%), 252(12%).

EXAMPLE 7

2-(1.4.5-Triphenylimidazol-2-yl mercapto)-octanoic acid

Similar to Example 6 from:
48 g of 2-(1.4.5-triphenylimidazol-2-yl mercapto)-octanoic acid ethyl ester in 500 cc. of ethanol,
11.5 g of sodium hydroxide in 100 cc. of ethanol.
The mixture is stirred for 8 hours at room temperature. Recrystallization of the crude acid from hexane/acetic acid ethyl ester.
Yield: 34 g F.: 108° C.
MS [m/e]: 470(33%), 426(13%), 328(100%), 269(54%), 252 (48%).

EXAMPLE 8

2-Methyl-2-(1.4.5-triphenylimidazol-2-yl mercapto)-propionic acid

Similar to Example 6 from:
32 g of 2-methyl-2-(1.4.5-triphenylimidazol-2-yl mercapto)-propionic acid ethyl ester in 1000 cc. of ethanol,
8.6 g of sodium hydroxide in 100 cc. of ethanol.
The mixture is refluxed for 4 hours.
Yield: 31.5 g F.: 189° to 191° C.
IR (in KBr): 1705 cm$^{-1}$.
MS [m/e]: 414(8.5%), 328(94%), 294(16%), 261(100%).

EXAMPLE 9

8-(1.4.5-Triphenylimidazol-2-yl mercapto)-octanoic acid sodium salt 12 g of 8-(1.4.5-triphenylimidazol-2-yl mercapto)-octanoic acid are dissolved in 250 cc. of 96% ethanol.

The equivalent amount of ethanolic sodalye (1 g of NaOH in 10 cc. of ethanol) is added and the mixture is stirred for a short time and evaporated to dryness in a vacuo. The residue is pulverized.

Yield: 12.1 g.
IR (in KBr): 1558 cm$^{-1}$.

EXAMPLE 10

4-(1.4.5-Triphenylimidazol-2-yl mercapto)-butyric acid sodium salt

Similar to Example 9 from:
70 g of 4-(1.4.5-triphenylimidazol-2-yl mercapto)-butyric acid in 1200 cc. of 96% ethanol,
6.7 g of NaOH in 67 cc. of ethanol.
Yield: 71.5 g.
IR (in KBr): 1561 cm$^{-1}$.

EXAMPLE 11

The sodium salt of 2-(1.4.5-triphenylimidazol-2-yl mercapto)-octanoic acid

Similar to Example 9 from:
24 g of 2-(1.4.5-triphenylimidazol-2-yl mercapto)-octanoic acid in 500 cc. of 96% ethanol,
2 g of NaOH in 20 cc. of ethanol.
Yield: 24.4 g.
IR (in KBr): 1604 cm$^{-1}$.

EXAMPLE 12

The sodium salt of 2-(1.4.5-triphenylimidazol-2-yl mercapto)-propionic acid

Similar to Example 9 from:
32 g of 2-methyl-2-(1.4.5-triphenylimidazol-2-yl mercapto)-propionic acid in 1000 cc. of 96% ethanol,
2.9 g of NaOH in 30 cc. of ethanol.
Yield: 32.5 g.
IR (in KBr): 1617 cm$^{-1}$.

Similar to Examples 9 to 12 the sodium salts of all other acids according to the present invention have been produced.

EXAMPLE 13

4-(1.4.5-Triphenylimidazol-2-yl sulfonyl)-butyric acid 15 g of 4-(1.4.5-triphenylimidazol-2-yl mercapto)-butyric acid are dissolved in 100 cc. of anhydrous acetic acid at 80° C. and 3.5 cc. of a 30% solution of hydrogen peroxide is added dropwise. The solution is stirred, until the acid starting product has been reacted completely. Upon cooling, the sulfone crystallized, is filtered off with suction, washed with little acetic acid and water and is dried in a vacuo.

Yield: 11.1 g F.: 202° to 204° C.
Ir (in KBr): 1720 cm$^{-1}$.
MS [m/e]: 446(27%), 295(100%), 268(20%).

EXAMPLE 14

The sodium salt of 4-(1.4.5-triphenylimidazol-2-yl sulfonyl)butyric acid

Similar to Example 9 from:
4-(1.4.5-Triphenylimidazol-2-yl sulfonyl)-butyric acid and NaOH in 96% ethanol.
IR (in KBr): 1575 cm$^{-1}$.

EXAMPLE 15

4-(1.4.5-Triphenylimidazol-2-yl sulfinyl)-butyric acid 20 g of 4-(1.4.5-triphenylimidazol-2-yl mercapto)-butyric acid are dissolved in 500 cc. of chloroform. A solution of 8.4 g of 3-chloroperbenzoic acid in 100 cc. of chloroform is added slowly and dropwise at 0° C. After stirring for 3 hours at 0° C., the chloroform solution is washed with water, dried over sodium sulfate and the solvent is evaporated in a vacuo. The residue is washed several times with ether and recrystallized from ethanol.

Yield: 13.1 g F.: 199° C.

What we claim is:

1. An imidazol-2-yl mercapto alkanoic acid having the formula I

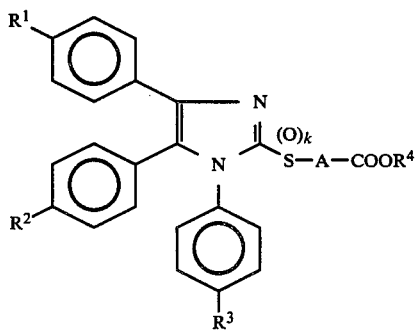

wherein
k is zero or the integer 1 or 2,
R$^1$, R$^2$ and R$^3$ which are the same or different from each other, are a member selected from the group consisting of hydrogen, fluorine, chlorine, methyl, methoxy and trifluoromethyl,
R$^4$ is a member selected from the group consisting of hydrogen, sodium, potassium, methyl, ethyl, propyl, isopropyl and butyl, and
A is a member selected from the group consisting of the groups

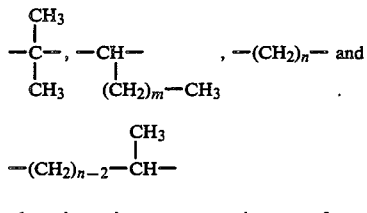

wherein m is zero or an integer from 1 to 8 and n is an integer from 2 to 10.

2. A compound of claim 1 wherein A is a member selected from the group consisting of the groups —(CH$_2$)$_3$— and

while k and R$^1$ and R$^4$ have the meanings as in claim 1.

3. A method for the treatment of a human suffering from an inflammatory disease or a disease in relation with his hyperlipidemic state wherein a compound as claimed in claim 1 or 2 is administered to said human in a dose between 1 and 1000 mg per day once or several times per day enterally or parenterally.

* * * * *